United States Patent
Buisker et al.

(10) Patent No.: US 11,674,109 B2
(45) Date of Patent: Jun. 13, 2023

(54) CLEANING AGENTS CONTAINING AMINE OXIDE AND COMPRISING SYNERGISTICALLY ACTING PROTEASES AND AMYLASES

(71) Applicant: Henkel AG & Co. KGaA, Duesseldorf (DE)

(72) Inventors: Detlef Buisker, Essen (DE); Marianne Schmeling, Korschenbroich (DE); Susanne Wieland, Dormagen/Zons (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 239 days.

(21) Appl. No.: 16/954,571

(22) PCT Filed: Oct. 24, 2018

(86) PCT No.: PCT/EP2018/079195
§ 371 (c)(1),
(2) Date: Jun. 17, 2020

(87) PCT Pub. No.: WO2019/120697
PCT Pub. Date: Jun. 27, 2019

(65) Prior Publication Data
US 2020/0332226 A1 Oct. 22, 2020

(30) Foreign Application Priority Data
Dec. 19, 2017 (DE) .................... 10 2017 223 275.7

(51) Int. Cl.
| | |
|---|---|
| *C11D 1/14* | (2006.01) |
| *C11D 1/29* | (2006.01) |
| *C11D 1/83* | (2006.01) |
| *C11D 1/90* | (2006.01) |
| *C11D 1/94* | (2006.01) |
| *C11D 3/386* | (2006.01) |
| *C11D 11/00* | (2006.01) |
| *C12N 9/28* | (2006.01) |
| *C11D 1/28* | (2006.01) |
| *C11D 1/75* | (2006.01) |

(52) U.S. Cl.
CPC ............ *C11D 1/94* (2013.01); *C11D 3/38618* (2013.01); *C11D 11/0023* (2013.01); *C12N 9/2417* (2013.01); *C11D 1/28* (2013.01); *C11D 1/75* (2013.01); *C11D 1/90* (2013.01)

(58) Field of Classification Search
CPC .. C11D 1/14; C11D 1/29; C11D 1/665; C11D 1/83; C11D 1/90; C11D 1/94; C11D 3/386; C11D 3/38618
See application file for complete search history.

(56) References Cited

U.S. PATENT DOCUMENTS

| | | | | |
|---|---|---|---|---|
| 2016/0355757 | A1* | 12/2016 | Lant .................... | C11D 3/38627 |
| 2017/0204352 | A1 | 7/2017 | Yan et al. | |
| 2019/0024020 | A1* | 1/2019 | Buisker ............... | C11D 3/38618 |

FOREIGN PATENT DOCUMENTS

| | | | | |
|---|---|---|---|---|
| WO | 2016203064 A2 | 12/2016 | | |
| WO | 2017097861 A1 | 6/2017 | | |
| WO | 2017162646 A1 | 9/2017 | | |
| WO | WO 2017/162646 | * | 9/2017 | ............. C11D 3/386 |

OTHER PUBLICATIONS

Buisker et al., Complete Sequence Listings for the enzymes disclosed in WO 2017/162646 (equivalent of US 2019/0024020), Sep. 28, 2017.*
International search report from parallel PCT Patent Application PCT/EP2018/079195 dated Apr. 30, 2019, 9 pages (for reference purposes only).

* cited by examiner

*Primary Examiner* — Brian P Mruk
(74) *Attorney, Agent, or Firm* — Viering Jentschura & Partner Mbb

(57) ABSTRACT

A cleaning composition may include at least one amine oxide, at least one fatty alcohol ether sulfate, an active protein of at least one amylase having at least 90% sequence identity with the amino acid sequence recited in SEQ ID NO:1 or SEQ ID NO:2, an active protein of at least one protease having at least 90% sequence identity with the amino acid sequence recited in SEQ ID NO:3 or SEQ ID NO:4, at least one betaine, optional additional substances and/or additives, and water.

20 Claims, No Drawings
Specification includes a Sequence Listing.

CLEANING AGENTS CONTAINING AMINE OXIDE AND COMPRISING SYNERGISTICALLY ACTING PROTEASES AND AMYLASES

CROSS-REFERENCE TO RELATED APPLICATIONS

The present application is a national stage entry according to 35 U.S.C. § 371 of PCT application No.: PCT/EP2018/079195 filed on Oct. 24, 2018; which claims priority to German Patent Application Serial No.: 10 2017 223 275.7, which was filed on Dec. 19, 2017; which are incorporated herein by reference in their entirety and for all purposes.

REFERENCE TO A SEQUENCE LISTING SUBMITTED VIA EFS-WEB

The content of the ASCII text file of the sequence listing named "P75591US_seq_ST25", which is 13 kb in size was created on Dec. 19, 2017 and electronically submitted via EFS-Web herewith the application is incorporated by reference in its entirety.

TECHNICAL FIELD

Cleaning agents may include amine oxide and specific amylases and proteases to act synergistically together for cleaning and/or disinfecting surfaces, in particular hard surfaces.

BACKGROUND

The use of amylases and proteases in cleaning agents per se is known. However, the cleaning performance of ordinary amylases and proteases in cleaning agents containing amine oxide is moderate. There is, however, a need for cleaning agents containing amine oxide which have an improved cleaning performance, in particular with respect to stains that contain starch and protein.

It is desirable to have an amine-oxide-based cleaning agent which shows improved cleaning performance with respect to stains that contain starch and protein.

SUMMARY

It has now surprisingly been found that a specific amylase having SEQ ID NO:1 and/or an amylase having SEQ ID NO:2 in combination with a specific protease having SEQ ID NO:3 and/or a protease having SEQ ID NO:4 in a cleaning agent containing amine oxide may be used for cleaning and/or disinfecting surfaces.

In a first aspect, a cleaning composition may include:
(a) 0.2 to 8 wt. % of at least one amine oxide;
(b) 5 to 20 wt. % of at least one fatty alcohol ether sulfate;
(c) $1 \times 10^{-8}$ to 5 wt. %, based on active protein, of at least one amylase having at least 90% sequence identity with the amino acid sequence given in SEQ ID NO:1 or SEQ ID NO:2 over the entire length;
(d) $1 \times 10^{-8}$ to 5 wt. %, based on active protein, of at least one protease having at least 90% sequence identity with the amino acid sequence given in SEQ ID NO:3 or SEQ ID NO:4 over the entire length;
(e) 0 to 10 wt. % of at least one betaine;
(f) 0 to 20 wt. % of additional substances and/or additives;
(g) 0 to 94.79 wt. % of water;
the sum of (a) to (g) being 100 wt. %.

DETAILED DESCRIPTION

"At least one," as used herein, refers to 1 or more, for example 2, 3, 4, 5, 6, 7, 8, 9 or more. In connection with components of the composition described herein, this information does not refer to the absolute amount of molecules, but to the type of the component. "At least one fatty alcohol ether sulfate" therefore means, for example, one or more different types of fatty alcohol ether sulfates. Together with amounts, the amounts refer to the total amount of the corresponding designated type of ingredient.

Unless otherwise indicated, all amounts indicated in connection with the agents described herein refer to wt. %, in each case based on the total weight of the composition. Moreover, amounts that relate to at least one component always relate to the total amount of this type of component contained in the composition, unless explicitly indicated otherwise. This means that specified amounts of this type, for example in connection with "at least one linear alkylbenzene sulfonate," refer to the total amount of linear alkylbenzene sulfonate contained in the composition.

Unless explicitly stated otherwise, the number-average and weight-average molecular weights are determined by means of gel permeation chromatography (GPC) using polystyrene standards.

The cleaning agent has at least one amine oxide. The cleaning agent contains 0.2 to 8 wt. %, in particular 0.3 to 7 wt. %, such as 0.5 to 6 wt. % of at least one amine oxide, based on the total weight of the cleaning agent.

Amine oxides that are suitable include alkyl amine oxides, in particular alkyl dimethyl amine oxides, alkyl amido amine oxides, and alkoxy alkyl amine oxides. Non-limiting amine oxides satisfy formula II or III,

$$R^6R^7R^8N^+\!-\!O^- \quad (II) \text{ or}$$

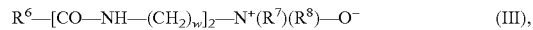
$$R^6\!-\![CO\!-\!NH\!-\!(CH_2)_w]_2\!-\!N^+(R^7)(R^8)\!-\!O^- \quad (III),$$

in which
$R^6$ is a saturated or unsaturated $C_{6-22}$ alkyl group, such as a $C_{8-18}$ alkyl group, in particular a saturated $C_{10-16}$ alkyl group, for example a saturated $C_{12-14}$ alkyl group which is bonded to the nitrogen atom N via a carbonylamidoalkylene group $-\!CO\!-\!NH\!-\!(CH_2)_2\!-$ in the alkyl amido amine oxides and via an oxaalkylene group $-\!O\!-\!(CH_2)z\!-$ in the alkoxy alkyl amino oxides, where z in each case represents a number from 1 to 10, such as 2 to 5, in particular 3, wherein w in each case represents a number from 0 to 5, such as 0 to 2, in particular 0 or 1, and $R^7$ and $R^8$ are, independently of one another, a $C_{1-4}$ alkyl group, optionally hydroxy-substituted, such as a hydroxyethyl group, in particular a methyl group.

Examples of suitable amine oxides are the following compounds: Amides, almond,N-[3-(dimethylamino)propyl]-,N-oxide; propane,1-dimethylamino-3-[(1-oxobabassu)amino]-,N-oxide; N,N-dimethyldocosylamine-N-oxide; amides, coco-,N-[3-(dimethylamino)propyl]; amines, coco alkyldimethyl-,N-oxide; morpholine,4-coco alkyl derivatives,4-oxide; N,N-dimethyldecylamine,N-oxide; 1-tetradecanamine,2-decyl-N,N-dimethyl-,N-oxide; 2,4-pyrimidinediamine,3-oxide; ethanol,2,2'-iminobis-,N-[3-($C_8$-$C_{10}$-alkyloxy)propyl] derivatives,N-oxide; ethanol,2,2'-iminobis-,N-[3-($C_9$-$C_{11}$-alkyloxy)propyl] derivatives,N-oxide; ethanol,2,2'-iminobis-,N-[3-($C_{12}$-$C_{15}$-alkyloxy) propyl] derivatives,N-oxide; ethanol,2,2'-iminobis-,N-coco alkyl derivatives,N-oxide; dodecylamine,N,N-bis(2-hydroxyethyl)-,N-oxide; ethanol,2,2'-(octadecylimino)bis-,N-oxide; ethanol,2,2'-iminobis-,N-tallow alkyl derivatives,N-oxide; amines, (hydrogenated palm kernel oil alkyl) dimethyl,N-oxide; amines, (hydrogenated tallow alkyl) dimethyl-,N-oxide; 1-propylamine,3-($C_{12}$-$C_{15}$-alkyloxy)-N-(2-hydroxyethyl)-N-(3-hydroxypropyl)-,N-oxide; isooctadecanamide,N-[3-(dimethylamino)propyl]-,N-oxide; isooctadecanamide,N-[3-(4-morpholinyl)propyl]-N-oxide; N-[3-(dimethylamino)propyl]dodecanamide-N-oxide; dodecyldimethylamine oxide; 4-methylmorpholine-4-oxide monohydrate; milk fat amides, N-[3-(dimethyloxidoamino)propyl]; 1,3-propanediamine, N,N-dimethyl-,N'-mink oil acyl derivatives,N-oxide; N-[3-(dimethylamino)propyl] myristamide-N-oxide; N,N-dimethyltetradecylamine-N-oxide; amines, N—($C_{14}$-$C_{16}$-alkyl)-N,N-dimethyl,N-oxide; N-[3-(dimethylamino)propyl]-9-octadecenamide-N-oxide; N,N-dimethyloleyl-N-oxide; olive oil amides, N-(3-dimethylaminopropyl)-,N-oxide; hexadecanamide, N-[(3-dimethylamino)propyl]-,N-oxide; hexadecyldimethylamine-N-oxide; α-hydro-ω-.ω'.-[(dodecyloxidoimino)di-poly(oxy-1,2-ethanediyl), (3 mol EO average molar ratio); phosphoric acid, monoesters with coco-alkylbis(2-hydroxyethyl)amine N-oxides, dipotassium salts; nitrilotris(methanephosphonic acid)-N-oxide, tripotassium salt; sesame oil amides, N-(3-dimethylaminopropyl)-,N-oxide; soy amides, N-[-3-(dimethylamino)propyl]-,N-oxide; N-[3-(dimethylamino)propyl] stearamide-N-oxide; N,N-dimethyloctadecylamine-N-oxide; tallow amides, N-[3-(dimethylamino)propyl]-,N-oxide; amine, tallow alkyl dimethyl, N-oxide; 10-undecenoamide,N-[3-(dimethylamino)propyl]-,N-oxide and wheat germ amides, N-(3-dimethylaminopropyl)-,N-oxide. The amine oxide is selected from cocamidopropylamine oxide, N-cocoalkyl-N,N-dimethylamine oxide, N-tallowalkyl-N,N-dihydroxyethylamine oxide, myristyl/cetyldimethylamine oxide or lauryldimethylamine oxide or mixtures thereof. A non-limiting amine oxide is, for example, cocamidopropylamine oxide (INCI: cocoamidopropylamine oxide).

The cleaning agent further contains one or more fatty alcohol ether sulfates. Fatty alcohol ether sulfates allow a stable foam volume in the presence of dirt, in particular fatty stains on the surfaces to be cleaned, or in water. Fatty alcohol ether sulfates are products of sulfation reactions on alkoxylated alcohols. A person skilled in the art generally understands alkoxylated alcohols to be the reaction products of alkylene oxide, such as ethylene oxide, with alcohols, such as with longer-chain alcohols, i.e. with aliphatic straight-chain or mono- or multi-branched, acyclic or cyclic, saturated or mono- or polyunsaturated, such as straight-chain, acyclic, saturated alcohols having 6 to 22, such as 8 to 18, in particular 10 to 16 or 12 to 14 carbon atoms. In general, n mol ethylene oxide and one mol alcohol results, depending on the reaction conditions, in a complex mixture of addition products having different degrees of ethoxylation (n=1 to 30, such as 1 to 20, in particular 1 to 10, or 2 to 4).

A further embodiment of the alkoxylation consists in using mixtures of the alkylene oxides, such as the mixture of ethylene oxide and propylene oxide. Non-limiting examples are low-ethoxylated fatty alcohols having 1 to 4 ethylene oxide units (EO), in particular 1 to 2 EO, for example 2 EO such as Na—$C_{12}$-$C_{14}$ fatty alcohols+2 EO sulfate.

The cleaning agent, in particular a hand dishwashing detergent, contains one or more fatty alcohol ether sulfates in an amount of from 5 to 20 wt. %, in particular from 6 to 16 wt. %, based on the total weight of the cleaning agent.

The total surfactant content of the cleaning agent is in the range of from 5.2 to 40 wt. %, in particular in the range of from 8 to 20 wt. %.

The cleaning agent further contains at least one amylase which has at least 90% sequence identity with the amino acid sequence given in SEQ ID NO:1 or SEQ ID NO:2 over the entire length. In various embodiments, the amino acid sequence has at least 90.5, 91, 91.5, 92, 92.5, 93, 93.5, 94, 94.5, 95, 95.5, 96, 96.2, 96.4, 96.6, 96.8, 97.0, 97.2, 97.4, 97.6, 97.8, 98.0, 98.2, 98.4, 98.6, 98.8, 99.0, 99.1, 99.2, 99.3, 99.4, 99.5, 99.6, 99.7, 99.8, 99.9, 01100.0% sequence identity with the amino acid sequence shown in SEQ ID NO:1 or SEQ ID NO:2 over the entire length. In various embodiments, the amylase consists of such a sequence, in particular of the sequence given in SEQ ID NO:1 or in SEQ ID NO:2.

In further embodiments, variants of these amylases are also included which are shorter than the N- and/or C-terminal sequences described above or are extended by 1-50 amino acids and/or have insertions, substitutions or deletions, but with the amylase activity being retained, in particular at least 70% of the activity of the non-shortened/non-extended/non-mutated enzyme.

In various embodiments, the cleaning agent may also contain a combination of two or more amylases, with each being as defined above. In particular, a first amylase can be contained which has at least 90% sequence identity with the acid sequence given in SEQ ID NO:1 over the entire length, and a second amylase which has at least 90% sequence identity with the amino acid sequence given in SEQ ID NO:2 over the entire length. All the embodiments generally disclosed above in connection with the amylases, in particular with regard to sequence identity and variants, are also applicable to any of the amylases in such a combination of two amylases.

The total content of these amylases is $1 \times 10^{-8}$ to 5 wt. % based on active protein. The amylases are contained in agents in an amount of from $1 \times 10^{-7}$ to 3 wt. %, from 0.00001 to 1 wt. %, from 0.00005 to 0.5 wt. %, from 0.0001 to 0.1 wt. %, or from 0.0001 to 0.05 wt. %, in each case based on active protein.

The cleaning agent further contains at least one protease which has at least 90% sequence identity with the amino acid sequence given in SEQ ID NO:3 or SEQ ID NO:4 over the entire length. In various embodiments, the amino acid sequence has at least 90.5, 91, 91.5, 92, 92.5, 93, 93.5, 94, 94.5, 95, 95.5, 96, 96.2, 96.4, 96.6, 96.8, 97.0, 97.2, 97.4, 97.6, 97.8, 98.0, 98.2, 98.4, 98.6, 98.8, 99.0, 99.1, 99.2, 99.3, 99.4, 99.5, 99.6, 99.7, 99.8, 99.9, or 100.0% sequence identity with the amino acid sequence shown in SEQ ID NO:3 or SEQ ID NO:4 over the entire length. In various embodiments, the protease consists of such a sequence, in particular of the sequence given in SEQ ID NO:3 or in SEQ ID NO:4.

In further embodiments, variants of these proteases are also included which are shorter than the N- and/or C-terminal sequences described above or are extended by 1-50 amino acids and/or have insertions, substitutions or deletions, but with the protease activity being retained, in particular at least 70% of the activity of the non-shortened/non-extended/non-mutated enzyme.

In various embodiments, the cleaning agent may also contain a combination of two or more proteases, with each being as defined above. In particular, a first protease can be contained which has at least 90% sequence identity with the amino acid sequence given in SEQ ID NO:3 over the entire length, and a second protease which has at least 90% sequence identity with the amino acid sequence given in SEQ ID NO:4 over the entire length. All the embodiments generally disclosed above in connection with the proteases, in particular with regard to sequence identity and variants, are also applicable to any of the proteases in such a combination of two proteases.

The total content of these proteases is $1 \times 10^{-8}$ to 5 wt. % based on active protein. The proteases are contained in agents in an amount from $1 \times 10^{-7}$ to 3 wt. %, from 0.00001 to 1 wt. %, from 0.00005 to 0.5 wt. %, from 0.0001 to 0.1 wt. %, or from 0.0001 to 0.05 wt. %, in each case based on active protein.

The protein concentration can generally be determined using known methods, for example the BCA method (bicinchoninic acid; 2,2'-bichinolyl-4,4'-dicarboxylic acid) or the Biuret method (A. G. Gornall, C. S. Bardawill and M. M. David, J. Biol. Chem., 177 (1948), p. 751-766). The active protein concentration can be determined in this regard by titrating the active centers using a suitable irreversible inhibitor and determining the residual activity (cf. M. Bender et al., J. Am. Chem. Soc. 88, 24 (1966), p. 5890-5913).

The identity of amino acid sequences is determined by a sequence comparison. This sequence comparison is based on the BLAST algorithm established and commonly used in the prior art (cf. for example Altschul, S. F., Gish, W., Miller, W., Myers, E. W. & Lipman, D. J. (1990): "Basic local alignment search tool," J. Mol. Biol. 215: 403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, p. 3389-3402) and occurs in principle by associating similar sequences of amino acids in the amino acid sequences. A tabular association of the positions concerned is referred to as alignment. Another algorithm available in the prior art is the FASTA algorithm. Sequence comparisons (alignments), in particular multiple sequence comparisons, are created using computer programs. The Clustal series, for example, is frequently used (cf. Chenna et al. (2003): Multiple sequence alignment with the Clustal series of programs. Nucleic Acid Research 31, 3497-3500), T-Coffee (cf. for example Notredame et al. (2000): T-Coffee: A novel method for multiple sequence alignments. J. Mol. Biol. 302, 205-217) or programs based on these programs or algorithms. Sequence comparisons (alignments) using the computer program Vector NTI® Suite 10.3 (Invitrogen Corporation, 1600 Faraday Avenue, Carlsbad, Calif., USA) with the predetermined default parameters, and the AlignX module of which for sequence comparisons is based on ClustalW, are also possible. Unless stated otherwise, the sequence identity given herein is determined by the BLAST algorithm.

Such a comparison also allows a statement regarding the similarity of the compared sequences. It is usually given in percent identity, i.e. the proportion of identical amino acid residues in said sequences or in an alignment of corresponding positions. The broader concept of homology takes conserved amino acid exchanges into account in the case of amino acid sequences, i.e. amino acids having similar chemical activity, since they usually perform similar chemical activities within the protein. Therefore, the similarity between the compared sequences can also be expressed in percent homology or percent similarity. Identity and/or homology information can be provided regarding whole polypeptides or genes or only regarding individual regions. Homologous or identical regions of different amino acid sequences are therefore defined by matches in the sequences. Such regions often have identical functions. They can be small and comprise only a few amino acids. Often, such small regions perform essential functions for the overall activity of the protein. It may therefore be expedient to relate sequence matches only to individual, optionally small regions. Unless stated otherwise, however, identity or homology information in the present application relates to the entire length of the particular amino acid sequence indicated.

Furthermore, the amylase/protease is a mature amylase/protease, i.e. the catalytically active molecule without signal peptide(s) and/or propeptide(s). Unless stated otherwise, the sequences given also each refer to mature (processed) enzymes.

In a non-limiting embodiment, the agent is a cleaning agent for hard surfaces, such as a liquid manual dishwashing detergent or an all-purpose cleaner. In particular, it is a hand dishwashing detergent which is used for manual dishwashing. In addition to amine oxide, fatty alcohol ether sulfate and the specific amylase(s) and protease(s), the agent may also contain one or more different anionic surfactants and/or non-ionic surfactants and/or one or more amphoteric surfactants and/or one or more cationic surfactants. With the exception of betaine (d), these are to be treated as a possible constituent of (f), i.e. as additives and/or additional substances. Exemplary compounds are explicitly set forth below under additives and/or additional substances.

The cleaning agent may optionally contain one or more betaines (d). Suitable betaines are the alkylbetaines, the alkylamidobetaines, the imidazolinium betaines, the sulfobetaines (INCI: sultaines) and the phosphobetaines and satisfy formula I,

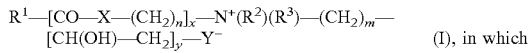

$R^1$ is a saturated or unsaturated $C_{6-22}$ alkyl group, preferably a $C_{8-18}$ alkyl group, in particular a saturated $C_{10-16}$ alkyl group, for example a saturated $C_{12-14}$ alkyl group,
X is NH, $NR^4$ with the $C_{1-4}$ alkyl group $R^4$, O or S,
n is a number from 1 to 10, such as 2 to 5, in particular 3,
x is 0 or 1, such as 1,
$R^2$ and $R^3$ are, independently of one another, a $C_{1-4}$ alkyl group, optionally hydroxy-substituted, such as a hydroxyethyl group, but in particular a methyl group, m is a number from 1 to 4, in particular 1, 2 or 3,
y is 0 or 1 and
Y is COO, $SO_3$, $OPO(OR^5)O$ or $P(O)(OR^5)O$, wherein $R^5$ is a hydrogen atom H or a $C_{1-4}$ alkyl group.
The alkyl and alkylamido betaines, betaines of formula I having a carboxylate group ($Y^- \equiv COO^-$) are also called carbobetaines.
Non-limiting betaines are the alkylbetaines of formula (Ia), the alkylamidobetaines of formula (Ib), the sulfobetaines of formula (Ic) and the amidosulfobetaines of formula (Id),

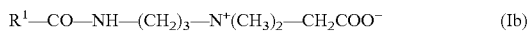

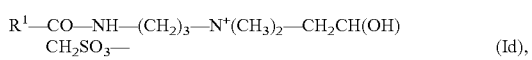

in which $R^1$ has the same meaning as in formula I.
Non-limiting betaines are the carbobetaines, in particular the carbobetaines of formulas (Ia) and (Ib), such as the alkylamidobetaines of formula (Ib).

Examples of suitable betaines and sulfobetaines are disclosed, for example, in WO 2008/046778 A1, to which reference is explicitly made. A non-limiting betaine is, for example, cocoamidopropyl betaine or betaine which is commercially available under the trade name Tego® Natural Betaine by Evonik.

The agent may contain one or more betaines in an amount from 0.5 to 10 wt. %, such as 0.75 to 9 wt. %, in particular 1 to 8 wt. %, based on the total weight of the cleaning agent.

Additives and/or Additional Substances (f)

The agent can contain up to 20 wt. %, based on the total weight of the cleaning agent, of additives and/or additional substances. Suitable additives and additional substances are listed below.

Substances that are also used as ingredients of cosmetic agents are also designated in the following according to the International Nomenclature of Cosmetic Ingredients (INCI) as appropriate. Chemical compounds have an INCI name in English. The INCI names can be found in the "International Cosmetic Ingredient Dictionary and Handbook, 7th Edition (1997)," which is published by The Cosmetic, Toiletry and Fragrance Association (CTFA), Washington D.C. (USA). The expression CAS means that the following numerical sequence is a designation of the Chemical Abstracts Service.

The anionic surfactants which are also optionally present in particular in hand dishwashing detergents include alkali salts of the fatty alcohol sulfate. The cleaning agent may have from 0.05 to 5 wt. %, in particular from 0.1 to 3 wt. %, such as from 0.3 to 1 wt. %, of the alkali salt of the fatty alcohol sulfate, of another anionic surfactant, based on the total weight of the cleaning agent. This can be used as an additional substance which affects the foam volume. It has been found that in the case of water having a water hardness of from 16 to 20° dH, that is to say in the case of hard water, a proportion of 0.05 wt. % and in particular a proportion of 0.1 wt. % is sufficient to achieve a foam volume that is only insubstantially reduced compared with soft water. The harder the water is, the higher the proportion of fatty alcohol sulfate ought to be. However, a proportion of more than 3 wt. %, in particular more than 5 wt. %, provides no further stabilization of the foam even in the case of very hard water having a water hardness of from 20 to 32° dH. It has been found that a proportion by weight of from 0.3 to 1 wt. % is sufficient to obtain the desired foam volume in both hard and very hard water having a water hardness of from 16 to 32° dH, in particular from 20 to 32° dH. A higher dosage of the alkali salt of the fatty alcohol sulfate would therefore only lead to an increase in costs, but not to a significantly larger foam volume.

The fatty alcohol sulfate has 12 to 14 C atoms, in particular 13 C atoms. The alkali salt is optionally a sodium salt. In particular, the alkali salt of the fatty alcohol sulfate is sodium lauryl sulfate. This can be used in a technically pure grade, so that, in addition to a fatty alcohol sulfate having 13 C atoms, a mixture of alkyl chains having a chain length from 12 to 14 carbon atoms is present. For example, a sodium lauryl sulfate, sold under the trade name Texapon® LS35 by BASF, can be used.

The anionic surfactants present in particular in hand dishwashing detergents also include alkyl sulfonates. The alkyl sulfonates (INCI: sulfonic acids) have an aliphatic straight-chain or mono- or multi-branched, acyclic or cyclic, saturated or mono- or polyunsaturated, such as branched, acyclic, saturated alkyl group having 6 to 22, such as 9 to 20, in particular 11 to 18 or 14 to 17 carbon atoms.

Suitable alkyl sulfonates are therefore the saturated alkane sulfonates, unsaturated olefin sulfonates and—formally derived from the alkoxylated alcohols which are also the basis for the alkyl ether sulfates—ether sulfonates, in which a distinction is made between terminal ether sulfonates (n-ether sulfonates) having a sulfonate function bonded to the polyether chain, and internal ether sulfonates (i-ether sulfonates) having a sulfonate function linked to the alkyl group. The alkane sulfonates, in particular alkane sulfonates having a branched, such as secondary alkyl group, for example the secondary alkane sulfonate sec. Na—$C_{13}$-$C_{17}$ alkane sulfonate (INCI: sodium $C_{14-17}$ alkyl sec sulfonate), are optional.

The cleaning agent may also have a linear alkylbenzene sulfonate or two or more linear alkylbenzene sulfonates as further anionic surfactant(s). The cleaning agent may contain these in 0.1 to 20 wt. %, in particular 1 to 10 wt. %, or 2 to 5 wt. %, based on the total weight of the cleaning agent. Linear alkylbenzene sulfonates usually also have an aliphatic straight-chain or mono- or multi-branched, acyclic, saturated or mono- or polyunsaturated alkyl side chain having 6 to 22, such as 8 to 20, in particular 10 to 16 and particularly such as 10 to 13 carbon atoms on the benzene ring, in addition to a sulfonic acid or sulfonate group. In embodiments these are the sodium salts of the linear alkylbenzene sulfonates.

Further possible anionic surfactants which can be used are known to a person skilled in the art from the relevant prior art relating to washing or cleaning agents. These include in particular aliphatic sulfates such as monoglyceride sulfates and ester sulfonates (sulfo fatty acid esters), lignosulfonates, fatty acid cyanamides, anionic sulfosuccinic acid surfactants, fatty acid isothionates, acylamino alkane sulfonates (fatty acid taurides), fatty acid sarcosinates, ether carboxylic acids and alkyl (ether) phosphates.

Suitable further anionic surfactants are also anionic gemini surfactants having a diphenyl oxide basic structure, two sulfonate groups and an alkyl group on one or both benzene rings according to formula (II): —$O_3S(C_6H_3R)O(C_6H_3R')SO_3$—, in which R represents an alkyl group having for example 6, 10, 12 or 16 carbon atoms and R' represents R or H (commercially available as Dowfax® Dry Hydrotrope Powder having $C_{16}$ alkyl group(s); INCI: sodium hexyldiphenyl ether sulfonate, disodium decyl phenyl ether disulfonate, disodium lauryl phenyl ether disulfonate, disodium cetyl phenyl ether disulfonate) and fluorinated anionic surfactants, in particular perfluorinated alkyl sulfonates such as ammonium $C_{9/10}$ perfluoroalkyl sulfonate (commercially available as Fluorad® FC 120) and perfluorooctanesulfonic acid potassium salt (commercially available as Fluorad® FC 95), there optionally being no fluorine compounds contained in the cleaning agents.

Non-limiting further anionic surfactants that are optionally contained are the anionic sulfosuccinic surfactants sulfosuccinates, sulfosuccinamates and sulfosuccinamides, in particular sulfosuccinates and sulfosuccinamates, such as sulfosuccinates. The sulfosuccinates are the salts of the monoesters and diesters of the sulfosuccinic acid HOOCCH($SO_3H$)$CH_2$COOH, while the sulfosuccinamates are understood to be the salts of the monoamides of the sulfosuccinic acid, and the sulfosuccinamides are understood to be the salts of the diamides of the sulfosuccinic acid. The salts are optionally alkali metal salts, ammonium salts and mono-, di- or trialkanolammonium salts, for example mono-, di- or triethanolammonium salts, in particular lithium, sodium, potassium or ammonium salts, e.g. sodium or ammonium salts, or sodium salts.

In the sulfosuccinates, one or both carboxyl groups of the sulfosuccinic acid are optionally esterified with one or two identical or different unbranched or branched, saturated or unsaturated, acyclic or cyclic, optionally alkoxylated alcohols having 4 to 22, such as 6 to 20, in particular 8 to 18, such as 10 to 16, such as 12 to 14 carbon atoms. Non-limiting examples are esters of unbranched and/or saturated and/or acyclic and/or alkoxylated alcohols, in particular unbranched, saturated fatty alcohols and/or unbranched, saturated, fatty alcohols alkoxylated with ethylene oxide and/or propylene oxide, such as ethylene oxide, and having a degree of alkoxylation of from 1 to 20, such as 1 to 15, in particular 1 to 10, such as 1 to 6, or 1 to 4. A non-limiting sulfosuccinate is sulfosuccinic acid lauryl polyglycol ester disodium salt (lauryl-EO-sulfosuccinate, di-Na salt, INCI: disodium laureth sulfosuccinate). In the sulfosuccinamates or sulfosuccinamides, one or both carboxyl groups of the sulfosuccinic acid optionally form a carboxylic acid amide together with a primary or secondary amine carrying one or two identical or different, unbranched or branched, saturated or unsaturated, acyclic or cyclic, optionally alkoxylated alkyl groups having 4 to 22, such as 6 to 20, in particular 8 to 18, such as 10 to 16, or 12 to 14 carbon atoms. Unbranched and/or saturated and/or acyclic alkyl groups, in particular unbranched, saturated fatty alkyl groups, are additional options. The sulfosuccinamates and sulfosuccinamides disclosed in WO 2008/046778 A1, to which reference is explicitly made, are also suitable. Yet another suitable sulfosuccinamate is disodium $C_{18-20}$ alkoxy propylene sulfosuccinamate.

Non-limiting anionic sulfosuccinic acid surfactants are imidosuccinate, mono-Na-sulfosuccinic acid di-isobutyl ester (commercially available as Monawet® MB 45), mono-Na-sulfosuccinic acid di-octyl ester (commercially available as Monawet® MO-84 R2W, Rewopol® SB DO 75), mono-Na-sulfosuccinic acid di-tridecyl ester (commercially available as Monawet® MT 70), fatty alcohol polyglycol sulfosuccinate-Na—$NH_4$ salt (commercially available as sulfosuccinate S-2), di-Na-sulfosuccinic acid mono-$C_{12/14}$-3EO ester (commercially available as Texapon® SB-3), sodium sulfosuccinic acid diisooctyl ester (commercially available as Texin® DOS 75) and di-Na-sulfosuccinic acid mono-C12/18 ester (commercially available as Texin® 128-P), in particular the mono-Na-sulfosuccinic acid di-octyl ester. In a particular embodiment, the cleaning agent contains one or more sulfosuccinates, sulfosuccinamates and/or sulfosuccinamides, such as sulfosuccinates and/or sulfosuccinamates, in particular sulfosuccinates, as anionic sulfosuccinic acid surfactants, in an amount usually of from 0.001 to 5 wt. %, such as 0.01 to 4 wt. %, in particular 0.1 to 3 wt. %, such as 0.2 to 2 wt. %, or 0.5 to 1.5 wt. %, for example 1 wt. %.

The amphoteric surfactants (zwitterionic surfactants) which can be used include alkylamido alkylamines, alkyl-substituted amino acids and acylated amino acids or biosurfactants.

Alkylamido Alkylamines

The alkylamido alkylamines (INCI: alkylamido alkylamines) are amphoteric surfactants of formula (III), $R^9$—CO—$NR^{10}$—$(CH_2)_i$—$N(R^{11})$—$(CH_2CH_2O)_j(CH_2)_k$—$[CH(OH)]_l$—$CH_2$—Z—OM (III), in which $R^9$ is a saturated or unsaturated $C_{6-22}$ alkyl group, such as a $C_{8-18}$ alkyl group, in particular a saturated $C_{10-16}$ alkyl group, for example a saturated $C_{12-14}$ alkyl group, $R^{10}$ is a hydrogen atom H or a $C_{1-4}$ alkyl group, such as H, i is a number from 1 to 10, such as 2 to 5, in particular 2 or 3, $R^{11}$ is a hydrogen atom H or $CH_2COOM$ (M is defined as follows), j is a number from 1 to 4, such as 1 or 2, in particular 1, k is a number from 0 to 4, such as 0 or 1, l is 0 or 1, wherein k=1 if l=1, Z is CO, $SO_2$, $OPO(OR^{12})$ or $P(O)(OR^{12})$, wherein $R^{12}$ is a $C_{1-4}$ alkyl group or M (defined as follows), and M is a hydrogen, an alkali metal, an alkaline earth metal or a protonated alkanolamine, for example protonated mono-, di- or triethanolamine.

Non-limiting representatives satisfy the formulas IIIa to IIId,

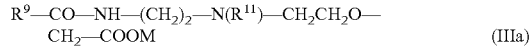

(IIIa)

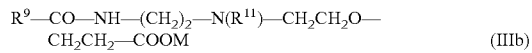

(IIIb)

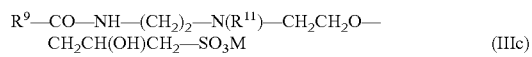

(IIIc)

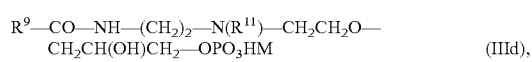

(IIId), in which $R^{11}$ and M have the same meaning as in formula (III).

Examples of suitable alkylamido alkylamines are e.g. those disclosed in WO 2008/046778 A1, to which reference is explicitly made.

Other suitable amphoteric surfactants are in particular N-2-hydroxyethyl-N-carboxymethyl fatty acid amidoethylamine-Na (commercially available as Rewoteric® AMV) and N-caprylic/capric amidoethyl-N-ethyl ether propionate-Na (commercially available as Rewoteric® AMVSF).

Alkyl-substituted amino acids

Non-limiting [[A]]alkyl-substituted amino acids are mono-alkyl-substituted amino acids of formula (IV),

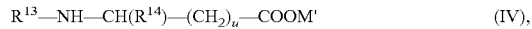

(IV), in which $R^{13}$ is a saturated or unsaturated $C_{6-22}$ alkyl group, such as a $C_{8-18}$ alkyl group, in particular a saturated $C_{10-16}$ alkyl group, for example a saturated $C_{12-14}$ alkyl group, $R^{14}$ is a hydrogen atom, H or a $C_{1-4}$-alkyl group, such as H, u is a number from 0 to 4, such as 0 or 1, in particular 1, and M' is a hydrogen, an alkali metal, an alkaline earth metal or a protonated alkanolamine, e.g. protonated mono-, di- or triethanolamine, alkyl-substituted imino acids according to formula (V),

(V), in which $R^{15}$ is a saturated or unsaturated $C_{6-22}$ alkyl group, such as a $C_{8-18}$ alkyl group, in particular a saturated $C_{10-16}$ alkyl group, for example a saturated $C_{12-14}$ alkyl group, v is a number from 1 to 5, such as 2 or 3, in particular 2, and M" is a hydrogen, an alkali metal, an alkaline earth metal or a protonated alkanolamine, for example protonated mono-, di- or triethanolamine, wherein M" in the two carboxy groups may have the same or two different meanings, for example, hydrogen and sodium or sodium in both cases, and mono- or dialkyl-substituted natural amino acids according to formula (VI),

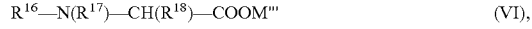

(VI), in which $R^{16}$ is a saturated or unsaturated $C_{6-22}$ alkyl group, such as $C_{8-18}$ alkyl group, in particular a saturated $C_{10-16}$ alkyl group, for example a saturated $C_{12-14}$ alkyl group, $R^{17}$ is a hydrogen atom or a $C_{1-4}$ alkyl group, optionally hydroxy- or amine-substituted, for example a methyl group, ethyl group, hydroxyethyl group or aminepropyl group.

$R^{18}$ is the group of one of the 20 natural α-amino acids $H_2NCH(R^{18})COOH$, and M''' is a hydrogen, an alkali metal, an alkaline earth metal or a protonated alkanolamine, e.g. protonated mono-, di- or triethanolamine.

Non-limiting alkyl-substituted amino acids are the aminopropionates according to formula (IVa),

$$R^{13}-NH-CH_2CH_2COOM' \quad (IVa),$$

in which $R^{13}$ and M' have the same meaning as in formula (IV).

Examples of suitable alkyl-substituted amino acids are disclosed in WO 2008/046778 A1, to which reference is explicitly made.

Acylated Amino Acids

Acylated amino acids are amino acids, in particular the 20 natural α-amino acids which carry the acyl group $R^{19}CO$ of a saturated or unsaturated fatty acid $R^{19}COOH$ on the amino nitrogen atom, wherein $R^{19}$ is a saturated or unsaturated $C_{6-22}$ alkyl group, such as a $C_{8-18}$ alkyl group, in particular a saturated $C_{10-16}$ alkyl group, for example a saturated $C_{12-14}$ alkyl group. The acylated amino acids can also be used as an alkali metal salt, alkaline earth metal salt or alkanolammonium salt, e.g. mono-, di- or triethanolammonium salt. Examples of acylated amino acids are those grouped together according to the INCI under amino acids: Acyl derivatives, e.g. sodium cocoyl glutamate, lauroyl glutamic acid, capryloyl glycine or myristoyl methylalanine.

In a further particular embodiment, the agent contains one or more amphoteric surfactants in an amount of more than 0.1 wt. % and less than 8 wt. %, such as less than 5 wt. %, less than 3 wt. %, based on the total weight of the cleaning agent.

Non-ionic surfactants that are optionally used are alkoxylated, advantageously ethoxylated, in particular primary alcohols having 8 to 18 C atoms and, on average, 1 to 12 mol ethylene oxide (EO) per mol of alcohol, in which the alcohol group can be linear or optionally methyl-branched in the 2 position, or can contain linear and methyl-branched groups in admixture, as are usually present in oxo alcohol groups. However, alcohol ethoxylates having linear groups of alcohols of native origin having 12 to 18 C atoms, for example of coconut, palm, tallow fatty or oleyl alcohol, and an average of 2 to 8 EO per mol of alcohol are additional options. Non-limiting ethoxylated alcohols include for example $C_{12-14}$ alcohols having 3 EO, 4 EO or 7 EO, $C_{9-11}$ alcohols having 7 EO, $C_{13-15}$ alcohols having 3 EO, 5 EO, 7 EO or 8 EO, $C_{12-18}$ alcohols having 3 EO, 5 EO or 7 EO, and mixtures thereof, such as mixtures of $C_{12-14}$ alcohol having 3 EO and $C_{12-18}$ alcohol having 7 EO. The degrees of ethoxylation indicated represent statistical averages that can correspond to an integer or a fractional number for a specific product. Non-limiting alcohol ethoxylates have a narrowed homolog distribution (narrow range ethoxylates, NRE). In addition to these non-ionic surfactants, fatty alcohols having more than 12 EO can also be used. Examples of these are tallow fatty alcohols having 14 EO, 25 EO, 30 EO, or 40 EO. Non-ionic surfactants that contain EO and PO groups together in the molecule can also be used. In particular, the cleaning agent for hard surfaces contains a C12-18 fatty alcohol having 7 EO or a C13-15 oxo alcohol having 7 EO as a non-ionic surfactant.

These non-ionic surfactants, in combination with an amine oxide, exhibit effective cleaning performance on fat-stained hard surfaces such as dishes.

Sugar surfactants which are also optionally contained in the cleaning agent are known surface-active compounds, which for example include the sugar surfactant classes of the alkyl glucose esters, aldobionamides, gluconamides (sugar acid amides), glycerol amides, glycerol glycolipids, polyhydroxy fatty acid amide sugar surfactants (sugar amides) and alkyl polyglycosides. Within the scope of the teaching, non-limiting sugar surfactants are the alkyl polyglycosides and the sugar amides and also derivatives thereof, in particular the ethers and esters thereof. The ethers are the products of the reaction of one or more, such as one, sugar hydroxy group with a compound containing one or more hydroxy groups, for example $C_{1-22}$ alcohols or glycols, such as ethylene and/or propylene glycol, it being possible for the sugar hydroxy group to also carry polyethylene glycol and/or polypropylene glycol groups. The esters are the reaction products of one or more, such as one, sugar hydroxy group with a carboxylic acid, in particular a $C_{6-22}$ fatty acid.

Non-limiting sugar amides satisfy the formula R'C(O)N(R'')[Z], in which R' represents a linear or branched, saturated or unsaturated acyl group, such as a linear unsaturated acyl group, having 5 to 21, such as 5 to 17, in particular 7 to 15, such as 7 to 13 carbon atoms, R'' represents a linear or branched, saturated or unsaturated alkyl group, such as a linear unsaturated alkyl group, having 6 to 22, such as 6 to 18, in particular 8 to 16, such as 8 to 14 carbon atoms, a $C_{1-5}$ alkyl group, in particular a methyl, ethyl, propyl, isopropyl, n-butyl, isobutyl, tert-butyl or n-pentyl group, or hydrogen, and Z represents a sugar residue, i.e. a monosaccharide residue. Non-limiting sugar amides are the amides of glucose, the glucamides, for example lauroyl-methyl-glucamide.

Alkyl Polyglycosides

The alkyl polyglycosides (APGs) are optional sugar surfactants within the scope of the teaching and satisfy the general formula $R'O(AO)_3[G]_x$, in which R' represents a linear or branched, saturated or unsaturated alkyl group having 6 to 22, such as 6 to 18, in particular 8 to 16, such as 8 to 14 carbon atoms, [G] represents a glycosidically linked sugar residue, and x represents a number from 1 to 10 and AO represents an alkylene oxy group, for example an ethylene oxy group or propylene oxy group, and a represents the average degree of alkoxylation from 0 to 20. Here, the group $(AO)_3$ can also contain different alkylene oxy units, for example ethylene oxy or propylene oxy units, with a then being the average overall degree of alkoxylation, i.e. the sum of degree of ethoxylation and degree of propoxylation. Unless stated otherwise hereinafter, the alkyl groups R' of the APGs are linear unsaturated groups having the specified number of carbon atoms.

APGs are non-ionic surfactants and constitute known substances which can be obtained in accordance with the relevant methods within the field of preparative organic chemistry. The index number x indicates the degree of oligomerization (DP degree), i.e. the distribution of mono- and oligoglycosides, and represents a number between 1 and 10. While x must always be an integer in a given compound, and can in particular assume the values x=1 to 6 here, for a particular alkyl glycoside the value x is an analytically determined, mathematical quantity, which is usually a fraction. Alkyl glycosides having an average degree of oligomerization x of from 1.1 to 3.0 are optionally used. With regard to the use, alkyl glycosides of which the degree of oligomerization is less than 1.7, and in particular is between 1.2 and 1.6, are optional. Xylose, but in particular glucose, is used as glycosidic sugar. The alkyl group or alkenyl group R' can be derived from primary alcohols having 8 to 18, such as 8 to 14, carbon atoms. Typical examples include caproic alcohol, caprylic alcohol, capric alcohol and undecyl alcohol as well as the industrial mixtures thereof, as obtained for example in the course of the hydrogenation of industrial fatty acid methyl esters or in the course of the hydrogenation of aldehydes in the Roelen oxosynthesis reaction.

The alkyl or alkenyl group R' is, however, derived from lauryl alcohol, myristyl alcohol, cetyl alcohol, palmoleyl alcohol, stearyl alcohol, isostearyl alcohol or oleyl alcohol. Further examples include elaidyl alcohol, petroselmyl alcohol, arachidyl alcohol, gadoleyl alcohol, behenyl alcohol, erucyl alcohol and the industrial mixtures thereof.

Non-limiting APGs are non-alkoxylated (a=0) and satisfy formula RO[G]$_x$, in which R, as before, represents a linear or branched, saturated or unsaturated alkyl group having 4 to 22 carbon atoms, [G] represents a glycosidically linked sugar residue, such as a glucose residue, and x represents a number from 1 to 10, such as 1.1 to 3, in particular 1.2 to 1.6. Accordingly, alkyl polyglycosides are, for example, $C_{8-10}$ and a $C_{12-14}$ alkyl polyglucoside having a DP degree of 1.4 or 1.5, in particular a $C_{8-10}$ alkyl-1,5-glucoside and a $C_{12-14}$ alkyl-1,4-glucoside.

Further suitable non-ionic surfactants are in particular $C_{10}$ dimethylamine oxide (commercially available as Ammonyx® DO), $C_{10-14}$ fatty alcohol+1.2PO+6.4EO (commercially available as Dehydol® 980), $C_{12/14}$ fatty alcohol+6EO (commercially available as Dehydol® LS6), $C_8$ fatty alcohol+1.2PO+9EO (commercially available as Dehydol® 010), $C_{16/20}$ Guerbet alcohol+8EO, n-butyl-capped (commercially available as Dehypon® G2084), mixture of a plurality of n-butyl-capped non-ionic surfactants and $C_{8/10}$ APG (commercially available as Dehypon® Ke 2555), $C_{8/10}$ fatty alcohol+1 PO+22EO-(2-hydroxydecyl)-ether (commercially available as Dehypon® Ke 3447), $C_{12/14}$ fatty alcohol+5EO+4PO (commercially available as Dehypon® LS 54 G), $C_{12/14}$ fatty alcohol+5EO+3PO, methyl-capped (commercially available as Dehypon® LS 531), $C_{12/14}$ fatty alcohol+10EO, n-butyl-capped (commercially available as Dehypon® LS 104 L), $C_{11}$ oxo alcohol+8EO (commercially available as Genapol® UD 088), $C_{13}$ oxoalcohol+8EO (commercially available as Genapol®x089), $C_{13/15}$ fatty alcohol EO adduct, n-butyl-capped (commercially available as Plurafac® LF 221) and alkoxylated fatty alcohol (commercial available as Tegotens® EC11).

The agent may additionally comprise one or more cationic surfactants (INCI: quaternary ammonium compounds). Non-limiting cationic surfactants are the quaternary surface-active compounds, in particular having an ammonium, sulfonium, phosphonium, iodonium or arsonium group, which are also known as antimicrobial active ingredients. By using quaternary surface-active compounds having an antimicrobial effect, the agent can be provided with an antimicrobial effect or the antimicrobial effect that may already be present due to other ingredients can be improved.

Non-limiting cationic surfactants are the quaternary ammonium compounds (QAC, INCI: quaternary ammonium compounds) according to general formula (R')(R'') (R''')(R'$^V$)N$^+$X$^-$, in which R' to R'$^V$ are the same or different $C_{1-22}$ alkyl groups, $C_{7-28}$ aralkyl groups or heterocyclic groups, wherein two or, in the case of aromatic bonding such as in pyridine, even three groups together with the nitrogen atom form the heterocycle, e.g. a pyridinium or imidazolinium compound, and X$^-$ represents halide ions, sulfate ions, hydroxide ions or similar anions. For optimum antimicrobial activity, such as at least one of the groups has a chain length of from 8 to 18, in particular 12 to 16, carbon atoms. QACs can be produced by reacting tertiary amines with alkalizing agents, for example methyl chloride, benzyl chloride, dimethyl sulfate, dodecyl bromide, but also ethylene oxide. The alkylation of tertiary amines having a long alkyl group and two methyl groups is particularly simple; the quaternization of tertiary amines having two long groups and one methyl group can also be carried out under mild conditions using methyl chloride. Amines having three long alkyl groups or hydroxy-substituted alkyl groups are less reactive, and are optionally quaternized with dimethyl sulfate, for example.

Suitable QACs are, for example, benzalkonium chloride (N-alkyl-N,N-dimethyl-benzylammonium chloride, CAS No. 8001-54-5), benzalkon B (m,p-dichlorobenzyl dimethyl-$C_{12}$-alkyl ammonium chloride, CAS No. 58390-78-6), benzoxonium chloride (benzyl-dodecyl-bis-(2-hydroxyethyl)-ammonium chloride), cetrimonium bromide (N-hexadecyl-N,N-trimethyl-ammonium bromide, CAS No. 57-09-0), benzetonium chloride (N,N-dimethyl-N-[2-[2-[p-(1,1,3,3-tetramethylbutyl)phenoxy]ethoxy]ethyl]-benzyl ammonium chloride, CAS No. 121-54-0), dialkyl dimethyl ammonium chloride such as di-n-decyl dimethyl ammonium chloride (CAS No. 7173-51-5-5), didecyl dimethyl ammonium bromide (CAS No. 2390-68-3), dioctyl dimethyl ammonium chloride, 1-cetylpyridinium chloride (CAS No. 123-03-5) and thiazoline iodide (CAS No 15764-48-1) and mixtures thereof. Non-limiting QACs are benzalkonium chlorides having Ca-1a alkyl groups, in particular $C_{12-14}$ alkyl benzyl dimethyl ammonium chloride. A non-limiting QAC is coco-pentaethoxymethylammonium methosulfate (INCI: PEG-5 cocomonium methosulfate, commercially available as Rewoquat® CPEM).

Further suitable cationic surfactants are, in particular, cationic surfactants which are compatible with anionic surfactants, such as quaternary ammonium compounds, for example coco-pentaethoxymethylammonium methosulfate (INCI: PEG-5 cocomonium methosulfate, commercially available as Rewoquat® CPEM).

In order to avoid possible incompatibilities of the cationic surfactants with the anionic surfactants contained, cationic surfactant that is as compatible as possible with anionic surfactant is used and/or as little cationic surfactant as possible is used or cationic surfactants are omitted entirely.

Other polymeric polycarboxylates are suitable as builders, which may likewise be contained in the cleaning agent. These are, for example, the alkali metal salts of polyacrylic acid or of polymethacrylic acid, for example those having a number-average molecular weight of from 600 to 750,000 g/mol. Suitable polymers are in particular polyacrylates, such as having a number-average molecular weight of from 1,000 to 15,000 g/mol. Due to their superior solubility, the short-chain polyacrylates, which have a number-average molecular weight of from 1,000 to 10,000 g/mol, and particularly such as from 1,000 to 5,000 g/mol, may in turn be usable from this group.

In addition, copolymeric polycarboxylates are suitable, in particular those of acrylic acid with methacrylic acid and of acrylic acid or methacrylic acid with maleic acid. To improve water solubility, the polymers can also contain allyl sulfonic acids, such as allyloxybenzene sulfonic acid and methallyl sulfonic acid, as monomer.

The agents may also contain further hydrolytic enzymes or other enzymes in a concentration that is expedient for the effectiveness of the agent. Agents which further comprise one or more further enzymes thus constitute a further embodiment. Further enzymes which can be used are all enzymes which can exhibit catalytic activity in the agent, in particular a lipase, cellulase, hemicellulase, mannanase, tannase, xylanase, xanthanase, xytoglucanase, β-glucosidase, pectinase, carrageenase, perhydrolase, oxidase, oxidoreductase or other proteases/amylases, which are different from the proteases/amylases used, as well as mixtures thereof. Furthermore, conventional enzyme stabilizers may be contained.

An organic solvent may optionally be present. The solvent is used in the context of the teaching as needed, in particular as a hydrotropic substance, viscosity regulator and/or additional cold stabilizer. It acts in a solubilizing manner in particular for surfactants and optional electrolytes as well as perfume and dye and thus contributes to their incorporation, prevents the formation of liquid-crystalline phases and contributes to the formation of clear products.

Non-limiting organic solvents are derived from the group of monohydric or polyhydric alcohols, alkanolamines or glycol ethers. The solvents are selected from ethanol, n-propanol or i-propanol, butanol, glycol, propanediol or butanediol, glycerol, diglycol, propyl diglycol or butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl ether, propylene glycol ethyl ether or propylene glycol propyl ether, dipropylene glycol methyl ether or dipropylene glycol ethyl ether, methoxytriglycol, ethoxytriglycol, butoxytriglycol, 1-butoxyethoxy-2-propanol, 3-methyl-3-methoxybutanol, propylene-glycol-t-butyl ether, and mixtures of these solvents. The proportion by weight of these organic solvents with respect to the total weight of the cleaning agent is 0.1 to 10 wt. %, such as 0.2 to 8.0 wt. % and in particular 0.5 to 5.0 wt. %.

A non-limiting organic solvent which is particularly effective in stabilizing enzymatic cleaning agents is glycerol, as well as 1,2-propylene glycol.

Suitable organic solvents are, for example, saturated or unsaturated, such as saturated, branched or unbranched $C_{1-20}$ hydrocarbons, such as $C_{2-15}$ hydrocarbons, having at least one hydroxy group and optionally one or more ether functions C—O—C, i.e. oxygen atoms interrupting the carbon atom chain.

Non-limiting organic solvents are the $C_{2-6}$ alkylene glycols and poly-$C_{2-3}$ alkylene glycol ethers that are optionally unilaterally etherified with a $C_{1-6}$ alkanol and have an average of 1 to 9 identical or different, such as identical, alkylene glycol groups per molecule, as well the Cis alcohols, such as ethanol, n-propanol or isopropanol, in particular ethanol.

Non-limiting solvents are the poly-$C_{2-3}$ alkylene glycol ethers that are unilaterally etherified with a $C_{1-6}$ alkanol and have an average of 1 to 9, such as 2 to 3, ethylene or propylene glycol groups, for example PPG-2 methyl ether (dipropylene glycol monomethyl ether).

As a solubilizer, in particular for optionally contained perfume and dyes, alkanolamines may also be used besides the solvents described above, for example.

In addition to the components mentioned so far, the agents may contain further ingredients. These include, for example, additives for improving the flow and drying behavior, for adjusting the viscosity, and for stabilization and other additional substances that are customary in hand dishwashing detergents, such as UV stabilizers, perfume, pearlescing agents, dyes, corrosion inhibitors, preservatives, disinfectants, pH adjusters and additives improving the feel of the skin, or nourishing additives.

Polymers that are suitable as additives are in particular maleic acid-acrylic acid copolymer Na salt (for example, commercially available Sokalan® CP 5 by BASF, Ludwigshafen (Germany)), modified polyacrylic acid Na salt (for example, commercially available Sokalan® CP 10 by BASF, Ludwigshafen (Germany)), modified polycarboxylate Na salt (for example, commercially available Sokalan® HP 25 by BASF, Ludwigshafen (Germany)), polyalkylene oxide, modified heptamethyltrisiloxane (for example, commercially available Silwet® L-77 by BASF, Ludwigshafen (Germany)), polyalkylene oxide, modified heptamethyltrisiloxane (for example, commercially available Silwet® L-7608 by BASF, Ludwigshafen (Germany)), as well as polyethersiloxane (copolymers of polymethyl siloxanes with ethylene oxide/propylene oxide segments (polyether blocks)), such as water-soluble, linear polyether siloxanes with terminal polyether blocks, such as the commercially available compounds Tegopren® 5840, Tegopren® 5843, Tegopren® 5847, Tegopren® 5851, Tegopren® 5863, or Tegopren® 5878 by Evonik, Essen (Germany). In a particular embodiment, the above-mentioned polymers are omitted.

Polymeric thickening agents which may also be present in the cleaning agent are the polycarboxylates which have a thickening action as polyelectrolytes, such as homo- and copolymerizates of acrylic acid, in particular acrylic acid copolymers such as acrylic acid-methacrylic acid copolymers, and the polysaccharides, in particular heteropolysaccharides, and other conventional thickening polymers.

Suitable polysaccharides or heteropolysaccharides are the polysaccharide gums, for example gum arabic, agar, alginates, carrageenans and their salts, guar, guar gum, tragacanth, gellan, ramsan, dextran or xanthan and their derivatives, for example propoxylated guar, and mixtures thereof. Other polysaccharide thickeners, such as starches or cellulose derivatives, may alternatively be used in addition to a polysaccharide gum, for example starches of various origins and starch derivatives, for example hydroxyethyl starch, starch phosphate esters or starch acetates, or carboxymethyl cellulose or its sodium salt or methyl, ethyl, hydroxyethyl, hydroxypropyl, hydroxypropyl methyl or hydroxyethyl methyl cellulose or cellulose acetate.

A polymeric thickener is the microbial anionic heteropolysaccharide xanthan gum which is produced from *Xanthomonas campestris* and some other species under aerobic conditions with a molecular weight of 2-15×10$^6$ and is available, for example, from Kelco under the trade name Keltrol®, for example as a cream-colored powder Keltrol® T (transparent) or as white granules Keltrol® RD (readily dispersable).

Acrylic acid polymers suitable as polymeric thickening agents are, for example, high-molecular-weight homopolymers of acrylic acid (INCI: carbomer) cross-linked with a polyalkenyl polyether, in particular an allyl ether of sucrose, pentaerythritol or propylene, and also referred to as carboxyvinyl polymers. Such polyacrylic acids are available, inter alia, from BFGoodrich under the trade name Carbopol®, for example Carbopol® 940 (molecular weight $M_w$ approximately 4,000,000 g/mol), Carbopol® 941 (molecular weight $M_w$ approximately 1,250,000 g/mol) or Carbopol® 934 (molecular weight $M_w$ approximately 3,000,000 g/mol).

However, particularly suitable polymeric thickening agents are the following acrylic acid copolymers: (i) copolymers of two or more monomers from the group of acrylic acid, methacrylic acid and their simple esters, such as formed with $C_{1-4}$ alkanols (INCI: acrylates copolymer) which include, for example, the copolymers of methacrylic acid, butyl acrylate and methyl methacrylate (CAS 25035-69-2) or butyl acrylate and methyl methacrylate (CAS 25852-37-3) and which are available, for example, from Rohm & Haas under the trade names Aculyn® and Acusol®, for example the anionic non-associative polymers Aculyn® 33 (cross-linked), Acusol® 810 and Acusol® 830 (CAS 25852-37-3); (ii) cross-linked high-molecular-weight acrylic acid copolymers, which include for instance the copolymers of $C_{10-30}$ alkyl acrylates cross-linked with an allyl ether of sucrose or pentaerythritol with one or more monomers from the group of acrylic acid, methacrylic acid and their simple esters, such as formed with $C_{1-4}$ alkanols, (INCI acrylates/$C_{10-30}$ alkyl acrylate crosspolymer) and which are available, for example, from BFGoodrich under the trade name Carbopol®, for example the hydrophobized Carbopol® ETD2623 and Carbopol® 1382 (INCI: acrylates/$C_{10-30}$ alkyl acrylate crosspolymer) and Carbopol® AQUA 30 (formerly Carbopol® EX 473).

The content of polymeric thickening agent is usually not more than 8 wt. %, such as between 0.1 and 7 wt. %, such as between 0.5 and 6 wt. %, in particular between 1 and 5 wt. % and such as between 1.5 and 4 wt. %, for example between 2 and 2.5 wt. %. In a non-limiting embodiment, the cleaning agent is free of polymeric thickening agents.

The cleaning agent may contain one or more water-soluble salts to lower the viscosity. They may be inorganic and/or organic salts; in a non-limiting embodiment, the agent contains at least one inorganic salt.

Inorganic salts which can be used are selected from the group comprising colorless water-soluble halides, sulfates, sulfites, carbonates, hydrogen carbonates, nitrates, nitrites, phosphates and/or oxides of the alkali metals, alkaline earth metals, aluminum and/or transition metals; furthermore, ammonium salts can be used. Non-limiting examples are halides and sulfates of the alkali metals; the inorganic salt is therefore selected from the group comprising sodium chloride, potassium chloride, sodium sulfate, potassium sulfate and mixtures thereof.

The organic salts which can be used are, in particular, colorless water-soluble alkali metal, alkaline earth metal, ammonium, aluminum and/or transition metal salts of the carboxylic acids, including the dicarboxylic acids. In a non-limiting embodiment, the salts are selected from the group comprising formate, acetate, propionate, citrate, malate, maleate, tartrate, succinate, malonate, oxalate, lactate, fumarate, adipate, succinate, glutarate, methylglycinediacetic acid trisodium salt and mixtures thereof.

The cleaning agent may contain 1 to 10 wt. %, such as 2 to 8 wt. %, of at least one water-soluble salt. In a non-limiting embodiment, exclusively inorganic salts are used, in particular sodium chloride.

In addition, one or more further additional substances, in particular customary in hand dishwashing detergents and other cleaning agents for hard surfaces may also be contained, in particular UV stabilizers, perfume, pearlescing agents (INCI: opacifying agents; for example glycol distearate, for example the commercially available Cutina® AGS from Cognis, or mixtures containing same, for example the commercially available Euperlane® from Cognis), dyes, corrosion inhibitors, preservatives (for example the industrial 2-bromo-2-nitropropane-1,3-diol (CAS 52-51-7), also called bronopol, which is commercially available, for example, as Myacide® BT or Boots Bronopol BT from Boots), disinfectants, pH adjusters, in particular NaOH, KOH and buffer substances, as well as additives that improve the feel of the skin or nourishing additives (for example dermatologically active substances such as vitamin A, vitamin B2, vitamin B12, vitamin C, vitamin E, D-panthenol, sericerin, collagen partial hydrolyzate, various vegetable protein partial hydrolyzates, protein hydrolyzate fatty acid condensates, liposomes, cholesterol, vegetable and animal oils such as lecithin, soybean oil, etc., plant extracts such as aloe vera, azulene, witch hazel extracts, algae extracts, etc., allantoin, A.H.A. complexes) in amounts of usually not more than 5 wt. %.

Perfumes and Fragrances

In a non-limiting embodiment, the agent contains at least one perfume and/or at least one fragrance. It is possible to use all perfumes and/or fragrances known to a person skilled in the art, with the proviso that they do not substantially adversely affect the properties of the cleaning agent.

Microcapsules

It may be desirable to keep the active ingredients that positively affect the skin feel or also other sensitive active ingredients, such as perfumes, spatially separated from the actual agent until use. A convenient method for incorporating such sensitive, chemically or physically incompatible or volatile ingredients is the use of microcapsules, in which these ingredients are enclosed in a storage-stable and transport-stable manner and from which they are mechanically, chemically, thermally or enzymatically released for the purpose of or during use. In a non-limiting embodiment, therefore, one or more of the active ingredients that positively affect the skin feel and/or perfumes and/or fragrances is incorporated wholly or partly in microcapsules.

Microcapsules are finely dispersed liquid or solid phases coated with film-forming polymers, the preparation of which involves, after emulsification and coacervation or interfacial polymerization, the polymers precipitating on the material to be coated (active ingredient). In this case, the active ingredient is coated by a solid membrane in the manner of a shell (microcapsule in the narrower sense) or enclosed by a matrix (microsphere or sphere). In the following, the term microcapsule is used to cover both variants. Such capsules are usually microscopically small (<50 μm) and are sometimes also referred to as nanocapsules or nanospheres; they can be dried like powder. However, larger capsules or pearls visible to the naked eye (>0.5 mm) and filled with active ingredients can also be produced. Incorporated into the hand dishwashing detergent, these provide an additional visual appeal when the capsules are suspended in the agent in a stable and distributed manner, which can be achieved by selecting suitable surfactants and thickening agents and by setting a suitable viscosity.

As microcapsules, it is possible to use all surfactant-stable capsules and capsule materials or spheres and sphere materials available on the market, for example, the commercially available Primasphere® (chitosan and agar or carboxy methylcellulose) and Primasponge® (alginate, chitosan, agar) from BASF, Hallcrest Microcapsules® (gelatin, gum arabic) from Hallcrest, Inc. (US), Coletica Thalaspheres® (maritime collagen) from Coletica (FR), Lipotec Millicapseln® (alginic acid, agar-agar) from Lipotec S.A. (ES), Induchem Unispheres® (lactose, microcrystalline cellulose, hydroxypropyl methylcellulose) and Unicerin® C30 (lactose, microcrystalline cellulose, hydroxypropyl methylcellulose) from Induchem AG (CH), Kobo Glycospheres (modified starch, fatty acid esters, phospholipids) and Softspheres® (modified agar-agar) from Kobo (US) and Kuhs Probiol Nanospheres (phospholipids) from Kuhs (DE) and others. The microcapsules may have any shape in terms of production, but they are egg-shaped or ellipsoidal or in particular approximately spherical. Depending on the active ingredient and use in the agent, the diameter along its greatest spatial extent can be on average between 100 nm (not visually discernible as a capsule) and 10 mm. The average diameter is in the range of between 0.1 mm and 7 mm; microcapsules having an average diameter of between 0.4 mm and 5 mm are usable. To improve the appearance, dyes, color pigments or pearlescent components can also be added.

The active ingredient can be mechanically released from the microcapsules both by grinding the microcapsules during the cleaning process and by breaking up same by means of a suitable dosing device. Other options are releasing the active ingredient by changing the temperature (introduction into warm rinsing water), by shifting the pH, changing the electrolyte content, etc.

If microcapsules are used, their content is usually from 0.01 to 10 wt. %, such as from 0.1 to 5 wt. %, in particular from 0.2 to 3 wt. % or from 0.3 to 2 wt. %, it being possible for the cleaning agent to contain only similar microcapsules or else mixtures of different types of microcapsules.

The pH of the cleaning agent can be adjusted by means of customary pH regulators, for example acids, such as mineral acids or citric acid and/or alkalis, such as sodium or potassium hydroxide, with a range of from 4 to 9, such as 5 to 8.5, in particular 5.5 to 8.0, in particular for the desired skin and hand compatibility. To adjust and/or stabilize the pH, the agent may contain one or more buffer substances (INCI: buffering agents), usually in amounts of from 0.001 to 5 wt. %, such as 0.005 to 3 wt. %, in particular 0.01 to 2 wt. %, such as 0.05 to 1 wt. %, such as 0.1 to 0.5 wt. %, for example 0.2 wt. %. Buffer substances which are at the same time complexing agents or even chelating agents (chelators, INCI: chelating agents) are optionally usable.

The cleaning agent may also contain hydrotropic substances. These are solubilizers. Suitable hydrotropic substances are, for example, urea, butyl glycol or aliphatic short-chain anionic or amphoteric solubilizers.

The cleaning agent can be applied to the surface to be cleaned undiluted or as an aqueous dilution either directly or by means of a sponge or a brush, and then removed again using water. The cleaning agent is used for cleaning and/or disinfecting surfaces, such as hard surfaces, in particular dishes and cooking utensils.

In a non-limiting embodiment, the cleaning agent has a viscosity of at least 500 mPa·s, such as at least 1,000 mPa·s and/or the viscosity is at most 20,000 mPa·s, such as at most 10,000 mPa·s, measured by means of Brookfield DVII+ (small sample adapter, spindle SC4-31, T=20° C., shear rate $1.5\ s^{-1}$ (at 20,000 mPa·s) to $30\ s^{-1}$ (at 500 mPa·s to 1,000 mPa·s)).

EXAMPLES

The invention is described in the following with reference to examples, but is not limited thereto:

Various compositions were prepared and tested. The following table distinguishes between the example compositions (Ex.) and comparative example compositions (CEx.). Data are in wt. %.

| Component: | CEx. 1 | CEx. 2 | CEx. 3 | CEx. 4 | CEx. 5 | CEx. 6 | Ex. 7 | CEx. 8 |
|---|---|---|---|---|---|---|---|---|
| Amine oxide C12-18 | 2 | 2 | 2 | 2 | 2 | 2 | 2 | 2 |
| FAEOS C12-14 with 2EO | 9 | 9 | 9 | 9 | 9 | 9 | 9 | 9 |
| Cocamidopropyl betaine | 3 | 3 | 3 | 3 | 3 | 3 | 3 | 3 |
| Protease Progress Uno | | | | | | | | |
| Protease HET Ultra 1000L | | | | 0.1 | 0.3 | 0.6 | 0.3 | |
| Amylase Amplify Prime | 0.1 | 0.3 | 0.6 | | | | 0.3 | |
| Amylase Amplify 12 L | | | | | | | | 0.1 |
| Perfume | 0.2 | 0.2 | 0.2 | 0.2 | 0.2 | 0.2 | 0.2 | 0.2 |
| Dye | 0.01 | 0.01 | 0.01 | 0.01 | 0.01 | 0.01 | 0.01 | 0.01 |
| Preservative | 0.1 | 0.1 | 0.1 | 0.1 | 0.1 | 0.1 | 0.1 | 0.1 |
| Water | Up to 100 | Up to 100 | Up to 100 | Up to 100 | Up to 100 | Up to 100 | Up to 100 | Up to 100 |
| Performance | | 59 | 58 | | 41 | 43 | 66 | |

| Component: | CEx. 9 | CEx. 10 | Ex. 11 | CEx. 12 | CEx. 13 | CEx. 14 | Ex. 15 |
|---|---|---|---|---|---|---|---|
| Amine oxide C12-18 | 2 | 2 | 2 | 2 | 2 | 2 | 2 |
| FAEOS C12-14 with 2EO | 9 | 9 | 9 | 9 | 9 | 9 | 9 |
| Cocamidopropyl betaine | 3 | 3 | 3 | 3 | 3 | 3 | 3 |
| Protease Progress Uno | | | 0.3 | | | | |
| Protease HET Ultra 1000L | | | | 0.1 | 0.3 | 0.6 | 0.3 |
| Amylase Amplify Prime | | | | | | | 0.3 |
| Amylase Amplify 12 L | 0.3 | 0.6 | 0.3 | | | | |
| Perfume | 0.2 | 0.2 | 0.2 | 0.2 | 0.2 | 0.2 | 0.2 |
| Dye | 0.01 | 0.01 | 0.01 | 0.01 | 0.01 | 0.01 | 0.01 |
| Preservative | 0.1 | 0.1 | 0.1 | 0.1 | 0.1 | 0.1 | 0.1 |
| Water | Up to 100 | Up to 100 | Up to 100 | Up to 100 | Up to 100 | Up to 100 | Up to 100 |
| Performance % | 59 | 59 | 66 | | 42 | 45 | 69 |

FAEOS = Fatty alcohol ether sulfate

The detergent compositions were prepared and their cleaning performance checked:

Commercially available cheese sauce (Buitoni Quattro Formaggi) was evenly applied to porcelain plates and baked in an oven. After cooling to room temperature, the plates were weighed and soaked in an aqueous detergent solution (5 mL per liter of cold tap water) for 10 minutes. After this time, the plates were rinsed under running tap water. Subsequently, the plates were dried at room temperature and weighed again. For the respective example detergent compositions, the percentual amount of stain removed was calculated in %.

It can be clearly seen that the example compositions have an improved cleaning performance compared with the comparative examples and thus demonstrate a synergistic effect between amylase and protease.

The invention claimed is:

1. A cleaning composition comprising:
 (a) 0.2 to 8 wt. % of at least one amine oxide;
 (b) 5 to 20 wt. % of at least one fatty alcohol ether sulfate;
 (c) $1 \times 10^{-8}$ to 5 wt. %, based on active protein, of at least one amylase comprising at least 90% sequence identity with the amino acid sequence recited in SEQ ID NO:1 over the entire length;
 (d) $1 \times 10^{-8}$ to 5 wt. %, based on active protein, of at least one protease comprising at least 90% sequence identity with the amino acid sequence recited in SEQ ID NO:3 and/or SEQ ID NO:4 over the entire length;
 (e) 0 to 10 wt. % of at least one betaine;
 (f) 0 to 20 wt. % of additional substances and/or additives;
 (g) 0 to 94.78 wt. % water; wherein
 the sum of (a) to (g) is 100 wt. %.

2. The cleaning composition according to claim 1, wherein the at least one amine oxide ranges from 0.3 to 7 wt % and/or the at least one amine oxide is selected from alkly dimethyl amine oxide, alkyl amido amine oxide, alkoxy alkyl amine oxide, or mixtures thereof.

3. The cleaning composition according to claim 1, wherein the at least one fatty alcohol ether sulfate has 1 to 12 ethoxylate units and/or a C6 to C22 alkyl.

4. The cleaning composition according to claim 1, wherein the active protein of the at least one amylase is present in an amount ranging from $1 \times 10^{-7}$ to 3 wt. %.

5. The cleaning composition according to claim 1, wherein the active protein of the at least one protease is present in an amount ranging from $1 \times 10^{-7}$ to 3 wt. %.

6. The cleaning composition according to claim 1, wherein the at least one betaine ranges from 0.5 to 10 wt. %.

7. The cleaning composition according to claim 1, wherein the additional substances and/or additives are present in an amount ranging from 0.1 to 10 wt. % and are selected from the group consisting of perfumes, fragrances, dyes, preservatives, or mixtures thereof.

8. The cleaning composition according to claim 1, wherein the water is present in an amount ranging from 50 to 90 wt %.

9. The cleaning composition according to claim 1, wherein a pH ranges from 3 to 12.

10. The cleaning composition of claim 1, wherein the at least one amine oxide is present in an amount ranging from 0.5 to 6 wt. %.

11. The cleaning composition of claim 1, wherein the at least one fatty alcohol ether sulfate has 2 to 10 ethoxylate units.

12. The cleaning composition of claim 1, wherein the at least one fatty alcohol ether sulfate has a C8 to C18 alkyl.

13. The cleaning composition of claim 1, wherein the at least one betaine is present in an amount ranging from 0.75 to 9 wt. %.

14. The cleaning composition of claim 1, wherein the pH ranges from 6 to 8.

15. The cleaning composition of claim 1, further comprising a second amylase comprising at least 90% sequence identity with the amino acid sequence recited in SEQ ID NO:2 over the entire length.

16. The cleaning composition of claim 1, wherein the at least one protease comprises at least 90% sequence identity with the amino acid sequence recited in SEQ ID NO:3 over the entire length.

17. A cleaning composition comprising:
 (a) 0.2 to 8 wt. % of at least one amine oxide;
 (b) 5 to 20 wt. % of at least one fatty alcohol ether sulfate;
 (c) $1 \times 10^{-8}$ to 5 wt. %, based on active protein, of at least one amylase comprising at least 90% sequence identity with the amino acid sequence recited in SEQ ID NO:2 over the entire length;
 (d) $1 \times 10^{-8}$ to 5 wt. %, based on active protein, of at least one protease comprising at least 96% sequence identity with the amino acid sequence recited in SEQ ID NO:3;
 (e) 0 to 10 wt. % of at least one betaine;
 (f) 0 to 20 wt. % of additional substances and/or additives;
 (g) 0 to 94.78 wt. % water; wherein
 the sum of (a) to (g) is 100 wt. %.

18. The cleaning composition according to claim 17, further comprising at least a second protease comprising at least 90% sequence identity with the amino acid sequence recited in SEQ ID NO:4 over the entire length.

19. The cleaning composition according to claim 17, wherein the at least one protease comprises at least 97% sequence identity with the amino acid sequence recited in SEQ ID NO:3.

20. The cleaning composition according to claim 17, wherein the at least one protease comprises at least 97.6% sequence identity with the amino acid sequence recited in SEQ ID NO:3.

* * * * *

SEQUENCE LISTING

<160> NUMBER OF SEQ ID NOS: 4

<210> SEQ ID NO 1
<211> LENGTH: 482
<212> TYPE: PRT
<213> ORGANISM: Artificial
<220> FEATURE:
<223> OTHER INFORMATION: Amylase variant

<400> SEQUENCE: 1

His Asp Gly Thr Asn Gly Thr Ile Met Gln Tyr Phe Glu Trp Asn Val
1               5                   10                  15

Pro Asn Asp Gly Gln His Trp Asn Arg Leu His Asn Asn Ala Gln Asn
            20                  25                  30

Leu Lys Asn Ala Gly Ile Thr Ala Ile Trp Ile Pro Pro Ala Trp Lys
        35                  40                  45

Gly Thr Ser Gln Ser Asp Thr Gly Tyr Gly Ala Tyr Asp Leu Tyr Asp
    50                  55                  60

Leu Gly Glu Phe Asn Gln Arg Gly Thr Val Arg Thr Lys Tyr Gly Thr
65                  70                  75                  80

Lys Ala Glu Leu Glu Arg Ala Ile Arg Ser Leu Lys Ala Asn Gly Ile
                85                  90                  95

Gln Val Tyr Gly Asp Val Val Met Asn His Lys Ala Gly Ala Asp Gln
            100                 105                 110

Thr Glu Gln Val Gln Ala Val Glu Val Asn Pro Gln Asn Arg Asn Gln
        115                 120                 125

Glu Val Ser Gly Thr Tyr Gln Ile Glu Ala Trp Thr Gly Phe Asn Phe
    130                 135                 140

Pro Gly Arg Gly Asn Gln His Ser Ser Phe Lys Trp Arg Trp Tyr His
145                 150                 155                 160

Phe Asp Gly Thr Asp Phe Asp Gln Ser Arg Gly Leu Ser Asn Arg Ile
                165                 170                 175

Tyr Lys Phe Arg Thr Lys Ala Trp Asp Trp Glu Val Asp Thr Glu Phe
            180                 185                 190

Gly Asn Tyr Asp Tyr Leu Met Tyr Ala Asp Leu Asp Met Asp His Pro
        195                 200                 205

Glu Val Ile Asn Glu Leu Asn Arg Trp Gly Val Trp Tyr Ala Asn Thr
    210                 215                 220

Leu Asn Leu Asp Gly Phe Arg Leu Asp Ala Val Lys His Ile Lys Phe
225                 230                 235                 240

Ser Phe Met Arg Asp Trp Leu Gly His Val Arg Gly Gln Thr Gly Lys
                245                 250                 255

Asn Leu Phe Ala Val Ala Glu Tyr Trp Lys Asn Asp Leu Gly Ala Leu
            260                 265                 270

Glu Asn Tyr Leu Ser Lys Thr Asn Trp Thr Met Ser Ala Phe Asp Val
        275                 280                 285

Pro Leu His Tyr Asn Leu Tyr Gln Ala Ser Asn Ser Ser Gly Asn Tyr
    290                 295                 300

Asp Met Arg Asn Leu Leu Asn Gly Thr Leu Val Gln Arg His Pro Ser
305                 310                 315                 320

His Ala Val Thr Phe Val Asp Asn His Asp Thr Gln Pro Gly Glu Ala
                325                 330                 335

Leu Glu Ser Phe Val Gln Gly Trp Phe Lys Pro Leu Ala Tyr Ala Thr
            340                 345                 350

Ile Leu Thr Arg Glu Gln Gly Tyr Pro Gln Val Phe Tyr Gly Asp Tyr

```
                355                 360                 365
Tyr Gly Ile Pro Ser Asp Gly Val Pro Ser Tyr Arg Gln Gln Ile Asp
        370                 375                 380
Pro Leu Leu Ala Ala Arg Gln Gln Tyr Ala Tyr Gly Thr Gln His Asp
385                 390                 395                 400
Tyr Leu Asp Asn Gln Asp Val Ile Gly Trp Thr Arg Glu Gly Asp Ser
                405                 410                 415
Ala His Ala Gly Ser Gly Leu Ala Thr Val Met Ser Asp Gly Pro Gly
        420                 425                 430
Gly Ser Lys Thr Met Tyr Val Gly Thr Ala His Ala Gly Gln Val Phe
                435                 440                 445
Lys Asp Ile Thr Gly Asn Arg Thr Asp Thr Val Thr Ile Asn Ser Ala
        450                 455                 460
Gly Asn Gly Thr Phe Arg Cys Asn Lys Gly Ser Val Ser Ile Trp Val
465                 470                 475                 480
Lys Gln

<210> SEQ ID NO 2
<211> LENGTH: 483
<212> TYPE: PRT
<213> ORGANISM: Artificial
<220> FEATURE:
<223> OTHER INFORMATION: Amylase variant

<400> SEQUENCE: 2

His His Asn Gly Thr Asn Gly Thr Met Met Gln Tyr Phe Glu Trp Tyr
1               5                   10                  15
Leu Pro Asn Asp Gly Asn His Trp Asn Arg Leu Asn Ser Asp Ala Ser
                20                  25                  30
Asn Leu Lys Ser Lys Gly Ile Thr Ala Val Trp Ile Pro Pro Ala Trp
        35                  40                  45
Lys Gly Ala Ser Gln Asn Asp Val Gly Tyr Gly Ala Tyr Asp Leu Tyr
    50                  55                  60
Asp Leu Gly Glu Phe Asn Gln Lys Gly Thr Val Arg Thr Lys Tyr Gly
65                  70                  75                  80
Thr Arg Ser Gln Leu Gln Ala Ala Val Thr Ser Leu Lys Asn Asn Gly
                85                  90                  95
Ile Gln Val Tyr Gly Asp Val Val Met Asn His Lys Gly Gly Ala Asp
            100                 105                 110
Ala Thr Glu Met Val Arg Ala Val Glu Val Asn Pro Asn Asn Arg Asn
        115                 120                 125
Gln Glu Val Thr Gly Glu Tyr Thr Ile Glu Ala Trp Thr Arg Phe Asp
    130                 135                 140
Phe Pro Gly Arg Gly Asn Thr His Ser Ser Phe Lys Trp Arg Trp Tyr
145                 150                 155                 160
His Phe Asp Gly Val Asp Trp Asp Gln Ser Arg Arg Leu Asn Asn Arg
                165                 170                 175
Ile Tyr Lys Phe Arg Gly Lys Ala Trp Asp Trp Glu Val Asp Thr Glu
            180                 185                 190
Asn Gly Asn Tyr Asp Tyr Leu Met Tyr Ala Asp Ile Asp Met Asp His
        195                 200                 205
Pro Glu Val Val Asn Glu Leu Arg Asn Trp Gly Val Trp Tyr Thr Asn
    210                 215                 220
Thr Leu Gly Leu Asp Gly Phe Arg Ile Asp Ala Val Lys His Ile Lys
225                 230                 235                 240
```

```
Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Gln Lys Thr Asn Trp Asn His Ser Val Phe Asp
        275                 280                 285

Val Pro Leu His Tyr Asn Leu Tyr Asn Ala Ser Lys Ser Gly Gly Asn
    290                 295                 300

Tyr Asp Met Arg Asn Ile Phe Asn Gly Thr Val Val Gln Arg His Pro
305                 310                 315                 320

Ser His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Glu Gln Gly Tyr Pro Ser Val Phe Tyr Gly Asp
        355                 360                 365

Tyr Tyr Gly Ile Pro Thr His Gly Val Pro Ala Met Arg Ser Lys Ile
    370                 375                 380

Asp Pro Ile Leu Glu Ala Arg Gln Lys Tyr Ala Tyr Gly Pro Gln His
385                 390                 395                 400

Asp Tyr Leu Asp His Pro Asp Val Ile Gly Trp Thr Arg Glu Gly Asp
                405                 410                 415

Ser Ser His Pro Lys Ser Gly Leu Ala Thr Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys

<210> SEQ ID NO 3
<211> LENGTH: 269
<212> TYPE: PRT
<213> ORGANISM: Artificial
<220> FEATURE:
<223> OTHER INFORMATION: Protease variant

<400> SEQUENCE: 3

Ala Gln Ser Val Pro Trp Gly Ile Glu Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Arg Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110
```

```
Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Leu Leu Ser Thr Trp Pro Gly Ser Thr Tyr
        195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Asp Thr Trp Glu
                245                 250                 255

Tyr Gly Ser Gly Leu Val Asn Ala Glu Ala Ala Thr Arg
            260                 265

<210> SEQ ID NO 4
<211> LENGTH: 269
<212> TYPE: PRT
<213> ORGANISM: Artificial
<220> FEATURE:
<223> OTHER INFORMATION: Protease variant

<400> SEQUENCE: 4

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Glu Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Ile Gln Ser Thr Tyr Pro Gly Ser Thr Tyr
        195                 200                 205
```

-continued

```
Ala Ser Leu Asn Gly Thr Ser Met Ala Thr Pro His Val Ala Gly Ala
    210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
                260                 265
```